United States Patent
Imai et al.

(10) Patent No.: US 8,497,989 B2
(45) Date of Patent: Jul. 30, 2013

(54) PARTICLE COUNTING METHOD

(75) Inventors: Takehiro Imai, Tokyo (JP); Tomonobu Matsuda, Tokyo (JP); Toshiyuki Abe, Tokyo (JP); Tsutomu Nakajima, Tokyo (JP)

(73) Assignee: Rion Co., Ltd., Tokyo (JP)

( * ) Notice: Subject to any disclaimer, the term of this patent is extended or adjusted under 35 U.S.C. 154(b) by 0 days.

(21) Appl. No.: 13/307,318

(22) Filed: Nov. 30, 2011

(65) Prior Publication Data
US 2012/0133936 A1    May 31, 2012

(30) Foreign Application Priority Data
Nov. 30, 2010 (JP) ................................ 2010-266699

(51) Int. Cl.
*G01N 21/49*    (2006.01)
(52) U.S. Cl.
USPC ........................................................ 356/338
(58) Field of Classification Search
USPC ................... 356/335–343, 432–441
See application file for complete search history.

(56) References Cited

U.S. PATENT DOCUMENTS

| | | | | |
|---|---|---|---|---|
| 5,246,002 | A * | 9/1993 | Prosser | 600/336 |
| 5,365,559 | A * | 11/1994 | Hsueh et al. | 377/10 |
| 6,563,585 | B1 * | 5/2003 | Rao et al. | 356/436 |
| 6,678,049 | B1 * | 1/2004 | Painchaud | 356/432 |
| 7,268,874 | B2 * | 9/2007 | Brogioli et al. | 356/336 |

FOREIGN PATENT DOCUMENTS

| | | |
|---|---|---|
| JP | 11-258145 | 9/1999 |
| JP | 2006-177687 | 7/2006 |

* cited by examiner

*Primary Examiner* — Sang Nguyen
(74) *Attorney, Agent, or Firm* — Sheridan Ross P.C.

(57) ABSTRACT

A particle counting method that can count the number of the particles precisely. The method discriminates a wave pattern of the scattered light from a normal particle (subject of the counting) and a wave pattern of the light scattered by the agitation such as a floating particle, a radiation or changes in the intensity of the light. In one embodiment, a method for counting particles is disclosed which irradiates a light to a sample gas, detects a scattered light from a particle included in the sample gas by a photoelectric conversion device, counts the number of the particles of every particle size division by the output voltage wave pattern of the photoelectric conversion device, calculate a time difference (Ta–T1) from a point (T1) being a peak of output voltage wave pattern and a point (Ta) being a falling detection threshold (A), when the time difference (Ta–T1) is beyond counting cancellation time (B), the output voltage wave pattern is not counted as a particle.

4 Claims, 3 Drawing Sheets

PARTICLE COUNTING METHOD

FIELD OF THE INVENTION

This invention relates to a method of particle counting which counts the number of particles divided into particles of every size by irradiating a sample gas with light and detecting a scattered light from every particle contained in the sample gas.

BACKGROUND

In a production process in fields where it is necessary to work in a clean space, such as the semiconductor or electronic device industry, the work is carried out in a clean room. Therein, as a means to manage the clean room, a light scattering type particle counter is known, this counts the number of particles floating in the air.

The light scattering type particle counter is provided with a sensor block which detects a scattered light from a particle when a gas sample is irradiated with light from a light source. In this sensor block, an inlet nozzle and an outlet nozzle are disposed at a predetermined interval, an opened space exists between the inlet nozzle and the outlet nozzle, a linear flow path is formed in this space, and a sample gas flows from the inlet nozzle into the outlet nozzle through the flow path. In this type, a detection area is formed by irradiating the flow path with the light from a light source.

A slight turbulence may be generated in the flow path including the detection area, the particles which do not flow into the outlet nozzle are left in the sensor block, and drift in the sensor block. Such particles are called floating particles and the floating particles cause a false counting (miscalculation) in the particle detection.

To improve the false counting, Japanese Laid Open Patent No. Hei 11-258145 discloses a method to decrease false counting caused by floating particles (vagrancy particle), that is, to detect whether a wave pattern (a voltage wave pattern) of a particle is less than a baseline within a predetermined time, using the continuance time of the wave pattern of the atmospheric floating particle as being long.

Besides the false counting due to floating particles, a numerical value may be indicated even if a particle does not exist in a sample. This may be caused by a photoelectric conversion element (photodiode) reacting to an electromagnetic wave, a cosmic ray, whose radiation invades from the outside (it writes below down with radiations) or a change of the intensity of irradiation light.

To counteract such a false counting, Japanese Laid Open Patent No. 2006-177687 discloses a particle counter which subtracts a generation frequency of the false counting determined (calculated) beforehand from a counting after the start of measurement.

However, regarding the method disclosed in Japanese Laid Open Patent No. Hei 11-258145, if a duplicated wave pattern of a plurality of normal particles (subject of measurement) cannot be distinguished from the wave pattern of the floating particle, then it cannot count the number of the normal particles.

And, if it cannot distinguish the wave pattern due to radiation and a change of intensity of irradiation light, it may miscount by mistake.

Also, regarding the particle counter disclosed in Japanese Laid Open Patent No. 2006-177687, it does not take into consideration the floating particles, and subtracts the value that is predicted from generation frequency from measurements, it may be different from the actual value.

SUMMARY

Therein, the purpose of the present invention is to offer a counting method of the particle that can count the number of the particles precisely. Particularly, it discriminates between a wave pattern of the scattered light from a normal particle (subject of the counting) and a wave pattern of the scattered light by agitation such as a floating particle, radiation or changes in the intensity of light.

In order to solve the above-mentioned problems of one embodiment, the invention described herein irradiates a light to a sample gas, detects a scattered light from a particle included in the sample gas by a photoelectric conversion device, counts the number of the particles, every particle being divided by size, by the output voltage wave pattern of the photoelectric conversion device, Calculate a time difference (Ta–T1) with a point (T1) being a peak of output voltage wave pattern and a point (Ta) being a falling detection threshold (A), when the time difference (Ta–T1) exceeds a counting cancellation time (B), the output voltage wave pattern is not counted as a particle.

The invention of a second embodiment described herein, irradiates a light to a sample gas, detects a scattered light from a particle included in the sample gas by a photoelectric conversion device, counts the number of particles, every particle being divided by size, by the output voltage wave pattern of the photoelectric conversion device, The output voltage wave pattern has plural peaks, and a voltage value difference of each peak (Px) and the dip (Dx−1) just before the peak exceeds a predetermined voltage value (C), Calculate a time difference (Ta–Txm) with a point (Ta) being a falling detection threshold (A) and a point (Txm) being just before the peak (Pxm), when the time difference (Ta–Txm) exceeds a counting cancellation time (B), the output voltage wave pattern is not counted as a particle.

In a third embodiment of the invention described herein, when the voltage value difference of each peak (Px) and the dip (Dx−1) just before the peak does not exceed a predetermined voltage value (C), the output voltage wave pattern may be not counted as a particle.

In a fourth embodiment of the invention described herein, the falling detection threshold (A), the counting cancellation time (B) and the predetermined voltage value (C) may be modifiable.

The inventors of the present application discovered that the falling time of the output voltage wave pattern of the photoelectric conversion device corresponding to a floating particle, a radiation or a change of intensity of irradiation light is longer than that for a normal particle which is a subject to be counted.

And according to the present invention, it can count normal particles precisely by comparing this falling time, also, it is possible to distinguish a normal particle from a floating particle even if the output voltage wave pattern of the photoelectric conversion device is comprising a plurality of peaks.

DETAILED DESCRIPTION

Figure 1:
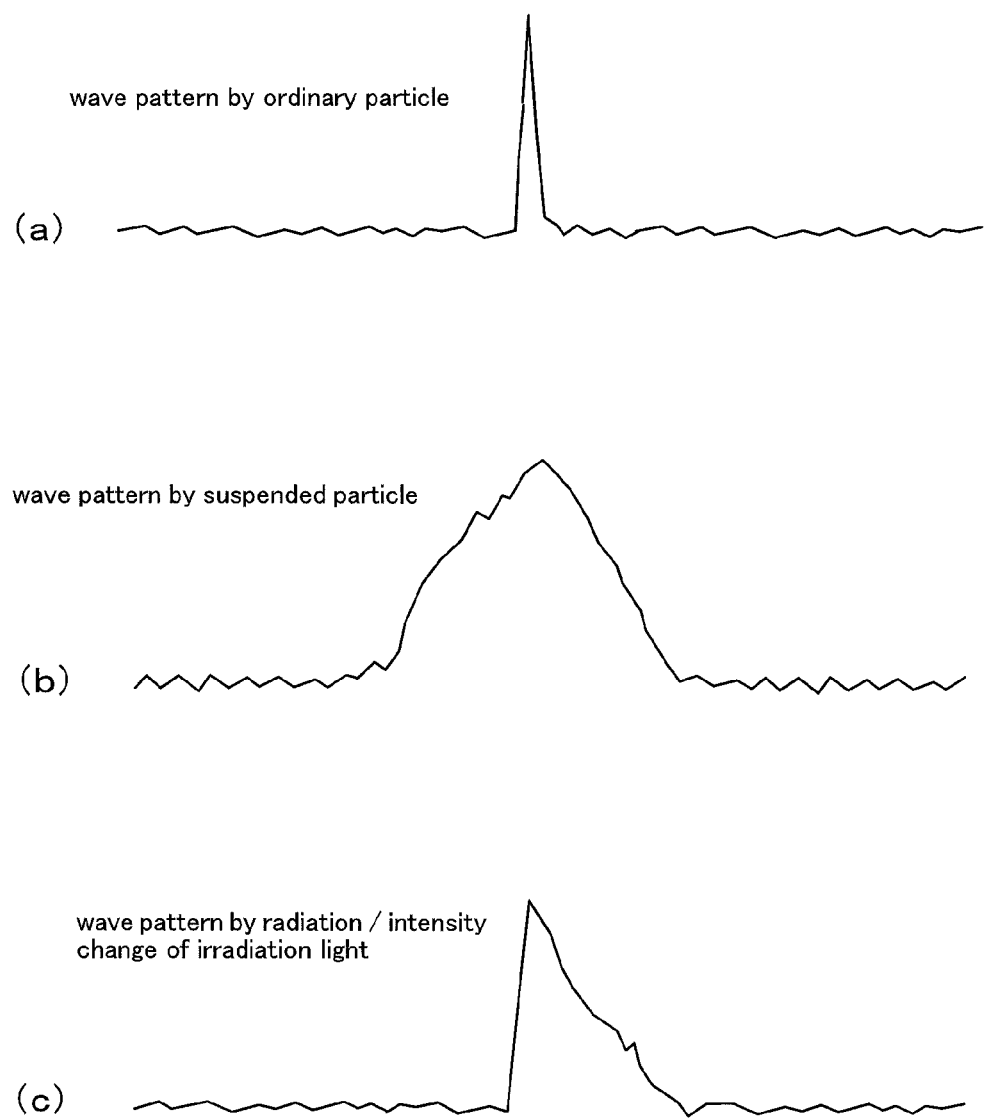
FIG. 1 shows an output voltage wave pattern of the photoelectric conversion device, (a) is a normal particle, (b) is a floating particle, (c) is a radiation or a change of intensity of irradiation light.

As shown FIG. 1, the output voltage wave pattern of the photoelectric conversion device corresponding to a floating particle, a radiation or a change of intensity of irradiation light is different from the output voltage wave pattern of a normal particle which is included in an air sample passing a detection area, so, it is possible to differentiate the particle types.

As shown in FIG. 1 (a), the output voltage wave pattern of the normal particle, rising time and falling time are almost the same (the boundary shape of the peak of the wave pattern is approximately symmetrical), the width (continuance time) of this wave pattern is determined by the speed of the sample air and the particle size.

In contrast, as shown in FIG. 1 (b), the continuance time of the wave pattern increases for a floating particle.

Also, a plurality of peaks may exist. As shown in FIG. 1 (c), for the wave pattern caused by a radiation or an intensity change of irradiation light, the rising time is short but the falling time from the peak is long. That is, it can differentiate the wave pattern caused by a normal particle, a floating particle, a radiation or a intensity change of irradiation light by the falling time from the peak.

Herein, the gas is not limited to air, even if it is nitrogen, carbon dioxide or an inert gas, it can differentiate equally well.

Figure 2:
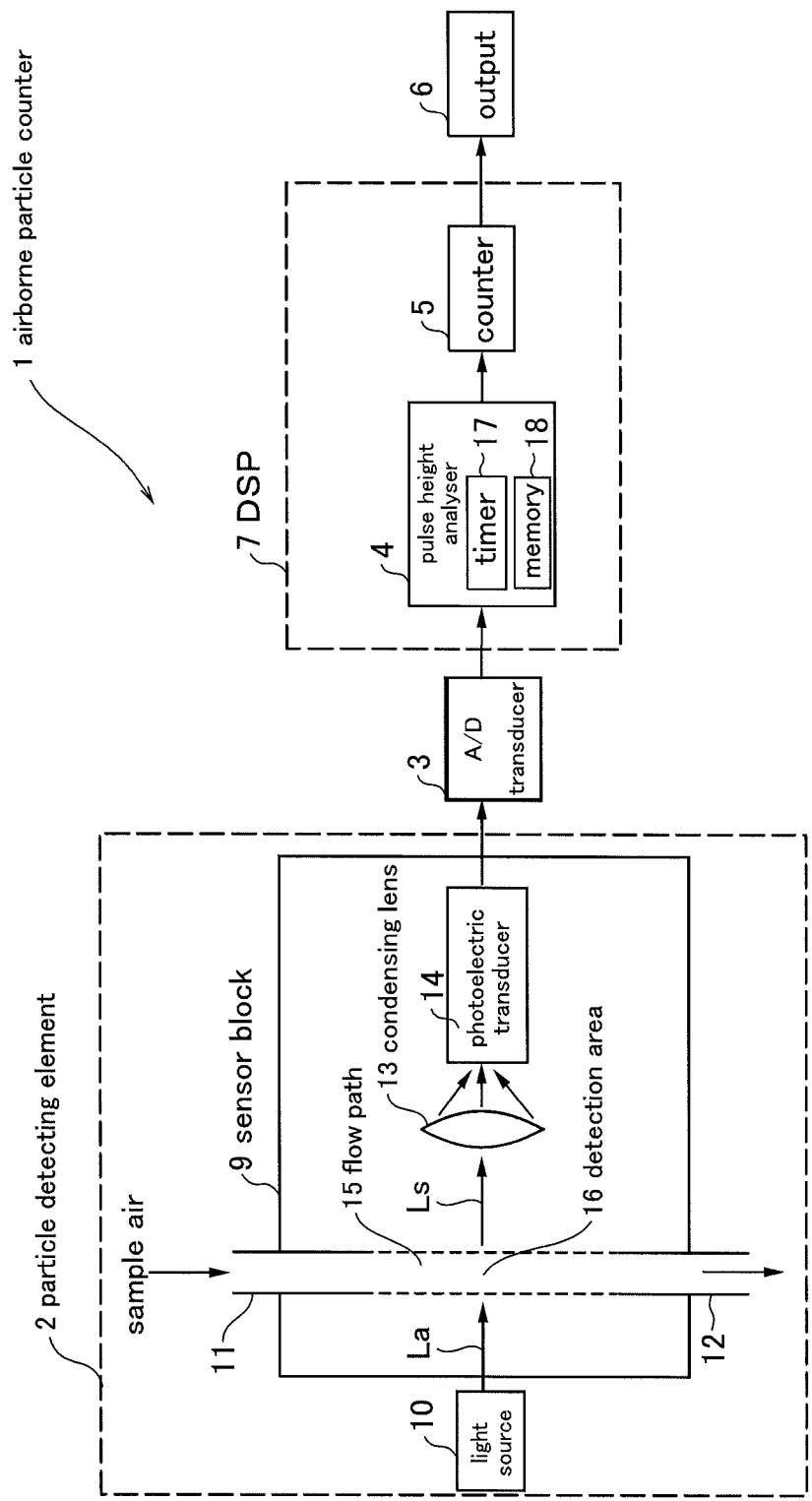
FIG. 2 shows a component of the a particle counter apparatus of the present invention which counts the number of particles in a gas.

As shown in FIG. 2, a particle counter apparatus 1 of the present invention is comprised of a particle detecting element 2, an A/D converter 3, a wave height analysis department 4, a counter 5 and an output 6.

The particle detecting element 2 is provided with a sensor block 9 and a source of light 10, an inlet nozzle 11 and an outlet nozzle 12 are disposed on the coaxial at a predetermined interval in the sensor block 9, and a condensing lens 13 and photoelectric conversion device 14 are provided in the sensor block 9.

A sample air flows from the inlet nozzle 11 into the outlet nozzle 12 passing a flow path 15, a detection area 16 is formed by irradiating a light (laser beam) La to flow path 15 from a source of light 10 (e.g., laser light source).

When a particle passes detection area 16, a scattered light Ls is generated, the scattered light Ls is condensed with a condensing lens 13 and led to a photoelectric conversion device 14.

In the photoelectric conversion device 14, a photoelectric conversion element receives scattered light Ls, and outputs the voltage (analog signal) proportional to the strength of scattered light Ls. This voltage (analog signal) is converted into a digital signal by the A/D converter 3.

In this embodiment, the inlet nozzle 11 and the outlet nozzle 12 are provided, however, the outlet nozzle 12 is not essential, for example, a vent not protruding from the sensor block 9 may be provided. When the vent is far from the detection area 16, the continuance time of the wave pattern of the floating particle tends to get longer.

According to the present invention, it can identify a floating particle when such a vent is provided.

The wave height analysis department 4 performs an identification treatment as to whether it is a normal particle or a floating particle based on the output voltage wave pattern data of the photoelectric conversion device 14 converted into digital signal by the A/D converter 3.

In addition, regarding the normal particle, it analyzes the particle size and sends the information of the division by particle size to the counter 5.

Also in the wave height analysis department 4, a timer 17 and a memory 18 are provided, the timer 17 measures an elapsed time of the falling, the memory 18 saves the data such as wave pattern data or calculation treatment of data as necessary.

A reference value R, a falling detection threshold (predetermined A value), a counting cancellation time (predetermined B value), a predetermined voltage value (predetermined C value) are set in the memory 18 beforehand, and these value are changeable from the outside.

Herein, the reference value R is a threshold to judge whether it intends for of the peak detection, decided by the smallest particle size of the measurement subject and a noise level, if an output voltage wave pattern is beyond reference value R, it intends for of the peak detection.

The falling detection threshold (predetermined A value) is a value to determine the end of time of the output voltage wave pattern, and can be set to suitably discriminate/differentiate. The falling detection threshold (predetermined A value) may prefer a small value to reference value R.

The counting cancellation time (predetermined B value) is a value set to compare the falling time.

The predetermined voltage value (predetermined C value) is a value set to remove the small change that noises bring from the peak.

The counter 5 counts a particle based on an output signal of wave height analysis department 4 for particles of every particle size division. The wave height analysis department 4 and the counter 5 may comprise the DSP (Digital Signal Processor) 7. The output 6 outputs the number of the particles of every particle size division which are counted in the counter 5.

Then, explained below is a condition to distinguish a floating particle from a normal particle, which is an object to be counted.

Figure 3:
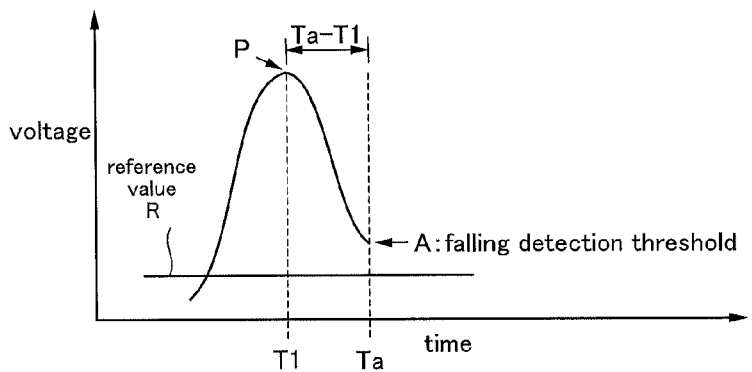
FIG. 3 explains an identification condition when the wave pattern has one peak.

As shown in FIG. 3, a line which represents the voltage beyond reference value R and become lower than falling detection threshold A, at this point, when the peak of the wave pattern is one, if a time difference (Ta−T1) with a point (Ta) of falling detection threshold (predetermined A value) and a point (T1) of peak P of the wave pattern exceeds the counting cancellation time (B), that is ((Ta−T1)>B), the output voltage wave pattern is not counted as a particle.

And if a time difference (Ta−T1) does not exceed the counting cancellation time (B), that is ((Ta−T1)<=B), the output voltage wave pattern is counted as a particle.

Figure 4:
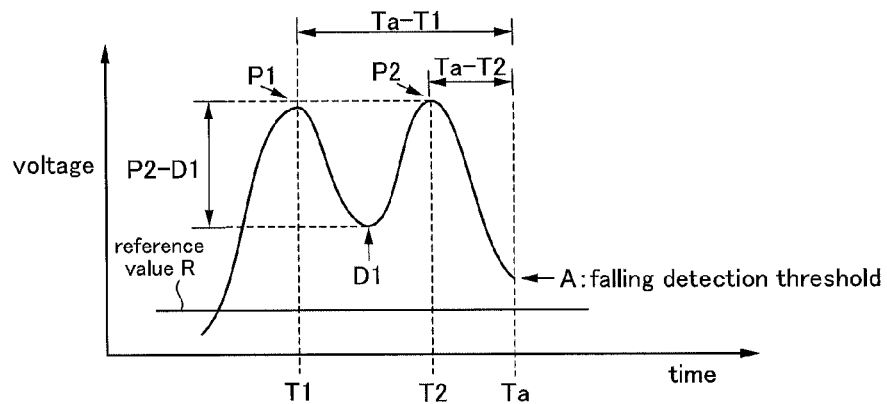
FIG. 4 explains an identification condition when the wave pattern has two peaks.

And as shown in FIG. 4, there are two peaks on the wave pattern at the point when the voltage line is beyond reference value R and becomes lower than falling detection threshold A, in the presence of the first dip (D1) between the first peak (P1) and the subsequent second peak (P2), calculate the voltage difference (P2−D1) between the first dip (D1) and the second peak (P2), and if the voltage difference (P2−D1) exceeds a predetermined voltage value (predetermined C value), take note of the second peak (P2).

When a time difference (Ta−T2) with point (T2) of the second peak (P2) and point (Ta) of the falling detection threshold (predetermined A value) exceeds the counting cancellation time (B), that is ((Ta−T2)>B), the output voltage wave pattern is not counted as a particle.

And if a time difference (Ta−T2) does not exceed the counting cancellation time (B), that is ((Ta−T2)<=B), the first peak (P1) and the second peak (P2) are counted as particles or the higher peak is counted as a particle. The decision on which to adopt is determined by the specifications of the apparatus.

When the voltage difference (P2−D1) does not exceed the predetermined voltage value (predetermined C value), the second peak (P2) is disregarded, and when a time difference (Ta−T1) with point (T1) of the second peak (P1) and point (Ta) of the falling detection threshold (predetermined A value) exceeds the counting cancellation time (B), that is ((Ta−T1)>B), the output voltage wave pattern is not counted as a particle.

And if the time difference (Ta−T1) does not exceed the counting cancellation time (B), that is ((Ta−T1)<=B), the first peak (P1) is counted as a particle.

Figure 5:
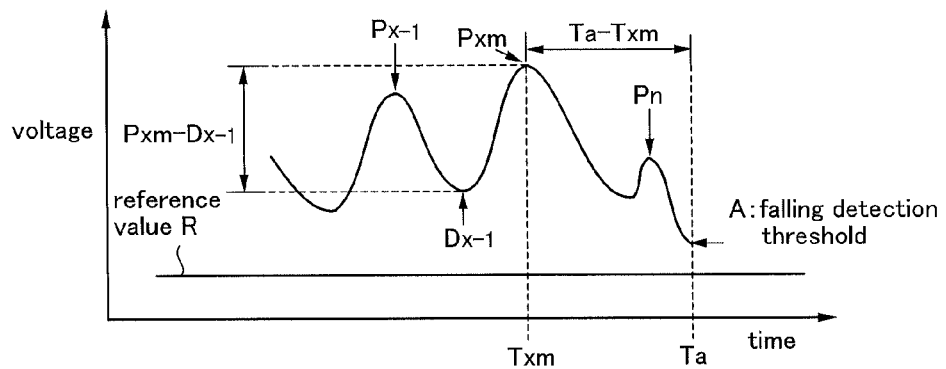
FIG. 5 explains an identification condition when the wave pattern has a plurality of peaks.

As shown in FIG. 5, there is a double peak on the wave pattern (n) at the point when the voltage line is beyond reference value R and becomes lower than the falling detection threshold A, and when a number of the peaks are m unit, the voltage difference with the dip which is right in front of each peak and the peak exceeds the predetermined voltage value (predetermined C value), take note of m-th peak (Pxm) that is close to (just before) the point in time of the falling detection threshold A.

When a time difference (Ta−Txm) with point (Txm) of the peak (Pxm) and point (Ta) of the falling detection threshold (predetermined A value) exceeds the counting cancellation time (B), that is ((Ta−Txm)>B), the output voltage wave pattern is not counted as a particle.

And in a case of ((Ta−Txm)<=B), the peaks (m) are counted as particles or the highest peak is counted as a particle. The decision on which it adopts is determined by the specifications of the apparatus.

Herein, the last peak (n) is ignored since the voltage difference does not exceed the predetermined voltage value (predetermined C value).

Explained below is a particle counting method of the present invention using the apparatus 1 comprised as above.

Sample an output voltage of photoelectric conversion device 14 that is an output signal of particle detecting element 2 by A/D converter 3 at a predetermined interval.

When a sampling value of the A/D converter 3 exceeds reference value R set beforehand, perform a comparison between the latest sampling value and sampling value to precede it.

Compare the preceding sampling value with the latest sampling value, and when a precedent sampling value becomes higher than the latest sampling value. it assume that a preceding sampling value is the first peak (P1).

After having determined the first peak (P1), compare the preceding sampling value with the latest sampling value, and when a precedent sampling value becomes smaller than the latest sampling value, it assume that a preceding sampling value is the first dip (D1).

After this, based on a condition of the identification, until the latest sampling value is lower than the falling detection threshold (a predetermined A value), detect peaks and dips by comparing the preceding sampling value with the latest sampling value over the whole of the wave pattern. And discriminate whether the wave pattern is a normal particle or a floating particle, when it is determined that it is the wave pattern of the floating particle, it is excluded from being an object for counting.

According to the present invention, it can count normal particles precisely by comparing the falling time of the output voltage wave pattern of the photoelectric conversion device, also, it is possible to distinguish a normal particle from a floating particle even if the output voltage wave pattern of the photoelectric conversion device is comprising a plurality of peaks.

As used herein, the following reference numbers generally correspond to the associated components:

1 . . . particle counter apparatus, 2 . . . particle detecting element, 3 . . . A/D converter, 4 . . . wave height analysis department, 5 . . . counter, 6 . . . output, 7 . . . DSP, 9 . . . sensor block, 10 . . . source of light, 11 . . . inlet nozzle, 12 . . . outlet nozzle, 13 . . . condensing lens, 14 . . . photoelectric conversion device, 16 . . . detection area, 17 . . . timer, 18 . . . memory, A . . . falling detection threshold, R . . . reference value.

The invention claimed is:

1. A method of particle counting, the method comprising:
irradiating a sample gas with a light;
detecting a scattered light from a particle included in the sample gas by a photoelectric conversion device;
counting a number of the particles of every particle size division by an output voltage wave pattern of the photoelectric conversion device; and
calculating, with a Digital Signal Processor (DSP), a time difference (Ta−T1) with a point (T1) of a peak of output voltage wave pattern and a point (Ta) of a falling detection threshold (A), when the time difference (Ta−T1) exceeds a counting cancellation time (B), the output voltage wave pattern is not counted as a particle.

2. A method of particle counting, the method comprising:
irradiating a sample gas with a light;
detecting a scattered light from a particle included in the sample gas by a photoelectric conversion device;
counting a number of the particles every particle size division by an output voltage wave pattern of the photoelectric conversion device, wherein the output voltage wave pattern has a plurality of peaks, and wherein a voltage value difference of each peak (Px) and a dip (Dx−1) just before that of the peak exceeds a predetermined voltage value (C); and
calculating, with a Digital Signal Processor (DSP), a time difference (Ta−Txm) with a point (Ta) of a falling detection threshold (A) and a point (Txm) just before that of the peak (Pxm), when the time difference (Ta−Txm) exceeds a counting cancellation time (B), the output voltage wave pattern is not counted as a particle.

3. A method of particle counting according to claim 2, wherein, when the voltage value difference of each peak (Px) and the dip (Dx−1) just before that of the peak does not exceed a predetermined voltage value (C), the peak of output voltage wave pattern is not a peak from a particle.

4. A method of particle counting according to any one of claims 1-3, wherein, the falling detection threshold (A), the counting cancellation time (B) and the predetermined voltage value (C) are modifiable.

* * * * *